US007801267B2

(12) United States Patent
Bindra et al.

(10) Patent No.: US 7,801,267 B2
(45) Date of Patent: Sep. 21, 2010

(54) METHOD AND SYSTEM FOR AUTO POSITIONING COMPRESSION MECHANISM IN A MAMMOGRAPHY SYSTEM

(75) Inventors: Gagan Bindra, Bhopal (IN); Guy Hersemeule, Saint Arnoult en yvelines (FR)

(73) Assignee: General Electric Co., Schenectady, NY (US)

( * ) Notice: Subject to any disclaimer, the term of this patent is extended or adjusted under 35 U.S.C. 154(b) by 84 days.

(21) Appl. No.: 12/257,123

(22) Filed: Oct. 23, 2008

(65) Prior Publication Data

US 2010/0104063 A1   Apr. 29, 2010

(51) Int. Cl.
- A61B 6/04 (2006.01)
- H05G 1/54 (2006.01)
- H05G 1/02 (2006.01)

(52) U.S. Cl. .................. 378/37; 378/117; 378/196; 378/208

(58) Field of Classification Search .................. 378/37, 378/117, 196, 208
See application file for complete search history.

(56) References Cited

U.S. PATENT DOCUMENTS

| 3,971,950 | A | | 7/1976 | Evans et al. | |
|---|---|---|---|---|---|
| 4,821,727 | A | * | 4/1989 | Levene et al. | 600/407 |
| 5,706,327 | A | | 1/1998 | Adamkowski et al. | |
| 6,928,315 | B1 | * | 8/2005 | Nachaliel | 600/407 |
| 6,999,554 | B2 | * | 2/2006 | Mertelmeier | 378/37 |
| 2008/0187095 | A1 | * | 8/2008 | Boone et al. | 378/37 |
| 2008/0221478 | A1 | * | 9/2008 | Ritchie et al. | 600/562 |
| 2009/0003519 | A1 | * | 1/2009 | Defreitas et al. | 378/37 |
| 2009/0304146 | A1 | * | 12/2009 | Ramsauer | 378/37 |

\* cited by examiner

*Primary Examiner*—Edward J Glick
*Assistant Examiner*—Thomas R Artman

(57) ABSTRACT

A method and system for auto positioning a compression mechanism in a mammography imaging system is disclosed herewith. The method comprises: automatically elevating the compression mechanism upon detection of a breast biopsy device. The breast biopsy device can be detected upon connecting the same to the mammography system or can be detected upon noticing the same on the vicinity of the mammography system. The compression mechanism includes: breast compressor, breast holding paddles and paddle holders.

13 Claims, 6 Drawing Sheets

METHOD AND SYSTEM FOR AUTO POSITIONING COMPRESSION MECHANISM IN A MAMMOGRAPHY SYSTEM

FIELD OF THE INVENTION

This invention relates generally to mammography methods and systems, and more particularly to, a method and system for automatically adjusting the position of a compression mechanism in a mammography system upon detecting the presence of a breast biopsy device.

BACKGROUND OF THE INVENTION

Mammography has earned a great deal of significance, as it's a method for detecting signs of breast cancer. Many times, biopsies are done using breast biopsy devices in association with mammography systems.

Generally, a breast biopsy is done using a breast biopsy device connected to a mammography system. The mammography system takes different images of a breast and, with reference to the same, the biopsy operation is performed. For imaging, the breast needs to be compressed and in a mammography system generally the breasts are compressed using a compression mechanism. However while carrying out the breast biopsy operation, a breast biopsy device is connected and the breasts are compressed by the breast biopsy device. In order to prepare for the biopsy, different views of image of breast need to be taken. Generally one Scout image and two angular images are taken at different degree angles. The image gantry along with the X-ray source in the mammography system is rotated to have different image acquisitions at different angles. However there are certain problems associated with the image gantry rotation.

In some cases, the compression mechanism connected to the image gantry may come in the way of breast biopsy device during image gantry rotation. This might result in a collision between the breast biopsy device and the compression mechanism. It may also be startling or scary for the patient to hear the sound of a collision while the biopsy is being performed, which may cause the patent to move and decrease the accuracy of the biopsy operation.

One solution for this problem is to adjust the compression mechanism manually such that the compression mechanism is elevated by the operator to avoid collision between the breast biopsy device and image gantry. However, the sound of adjusting the compression mechanism while the patient is undergoing biopsy operation may itself be startling or scary for the patient. Further the need of operating the compression mechanism manually during an acquisition or biopsy operation can result in breast or patient movements, requiring re-acquisition.

Further the operation of raising the compression mechanism manually is time consuming and may cause discomfort to the patient. Manual adjustment of the compression mechanism is also subject to error.

Thus there exists a need to provide a method and device for auto positioning a compression mechanism in a mammography system during a breast biopsy operation.

SUMMARY OF THE INVENTION

The above-mentioned shortcomings, disadvantages and problems are addressed herein which will be understood by reading and understanding the following specification.

One embodiment of the present invention provides a method of auto positioning a compression mechanism in a mammography imaging system. The method comprises: automatically moving the compression mechanism upon detection of a breast biopsy device.

In another embodiment, a breast biopsy workflow in a mammography system having a compression mechanism and a rotatable image gantry is disclosed. The system comprises: detecting the presence of a breast biopsy device; automatically elevating the compression mechanism upon detecting the presence of the breast biopsy device; imaging breast from different angles by rotating the image gantry; and performing the biopsy operation with the breast biopsy device.

In yet another embodiment, a positioning mechanism for a compression mechanism in a mammography imaging system comprises: a detection mechanism configured to detect the presence of a breast biopsy device; and a controlling mechanism connected to the detection mechanism, configured to control the position of the compression mechanism based on the output of the detection mechanism.

In yet another embodiment, a mammography imaging system is disclosed. The system comprises: an image gantry along with an X-ray source; an adjustable compression mechanism connected to the image gantry; a detachable breast biopsy device attachable to the system; and a processor configured to control the position of the compression mechanism with reference to the breast biopsy device.

In yet another embodiment, a computer-readable media having one or more computer readable medium for positioning a compression mechanism is disclosed. The media comprises: a routine for generating a trigger signal to elevate the position of a compression mechanism, upon detecting a breast biopsy device. The media further comprises a routine for detecting the breast biopsy device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Various embodiments of the present invention are directed to methods and systems for automatically adjusting the position of a breast compression mechanism, such as a breast compressor, a breast holding paddle, or a paddle holder, in a mammography system upon detection of a breast biopsy operation. The breast biopsy device is detected upon connecting the device to the mammography system or upon noticing the presence of the device in proximity of the mammography system.

In an embodiment, an improved workflow for a breast biopsy operation is suggested.

In an embodiment, a mammography system with a mechanism to auto position the compression mechanism, upon detecting a breast biopsy device is disclosed.

Although the invention is explained with reference to breast biopsy devices, the application of the method may be extended to various other devices that are attachable to the mammography imaging system at different stages of imaging, such as breast positioner or magnifier.

Figure 1:
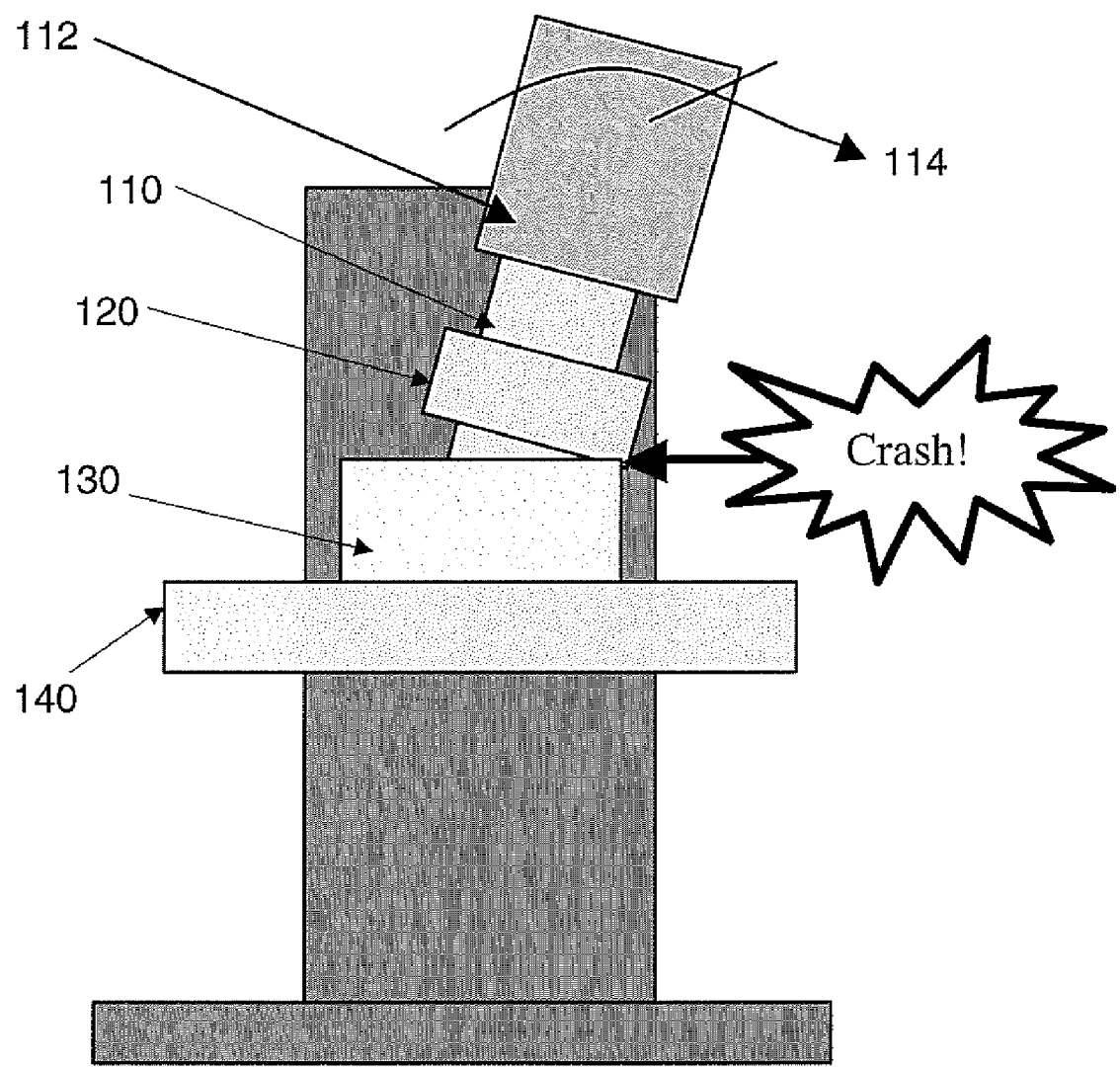
FIG. 1 is diagrammatic illustration of a mammography imaging system illustrating the problem solved by the invention.

FIG. 1 is diagrammatic illustration of a mammography imaging system illustrating the problem solved by the invention. The mammography imaging system comprises an image gantry 110, a compression mechanism 120 detachably connected to the image gantry 110 and a breast holder 140. A breast biopsy device 130 or some other similar external device may be connected to the mammography system as and when a biopsy operation is required. The breast biopsy device 130 is connected to the breast holder 140. In an example, before connecting the breast biopsy device, a part of the compression mechanism 120 may be removed.

Upon connecting the breast biopsy device 130, the compression mechanism 120 and the breast holder 140 remain at the same position. For performing the biopsy operation, images need to be taken from different angles. The image gantry 110 is rotated along with an X-ray source 112 located on the image gantry 110 and images are taken from different angles. The image gantry 110 is rotated to a certain angle 114, based on the requirement and the images are taken. While rotating the image gantry 110, the parts associated with the image gantry 110 such as compression mechanism 120 also rotate. When the image gantry 110 rotates at a certain angle 114, the compression mechanism 120 also rotates and may hit the breast biopsy device 130, which is stationary. This may cause damage to the breast biopsy device 130 or to the compression mechanism 120, and may startle or scare the patient and cause the patient to move. This is illustrated in FIG. 1. In an embodiment illustrated in FIG. 2, this problem is being addressed.

Figure 2:
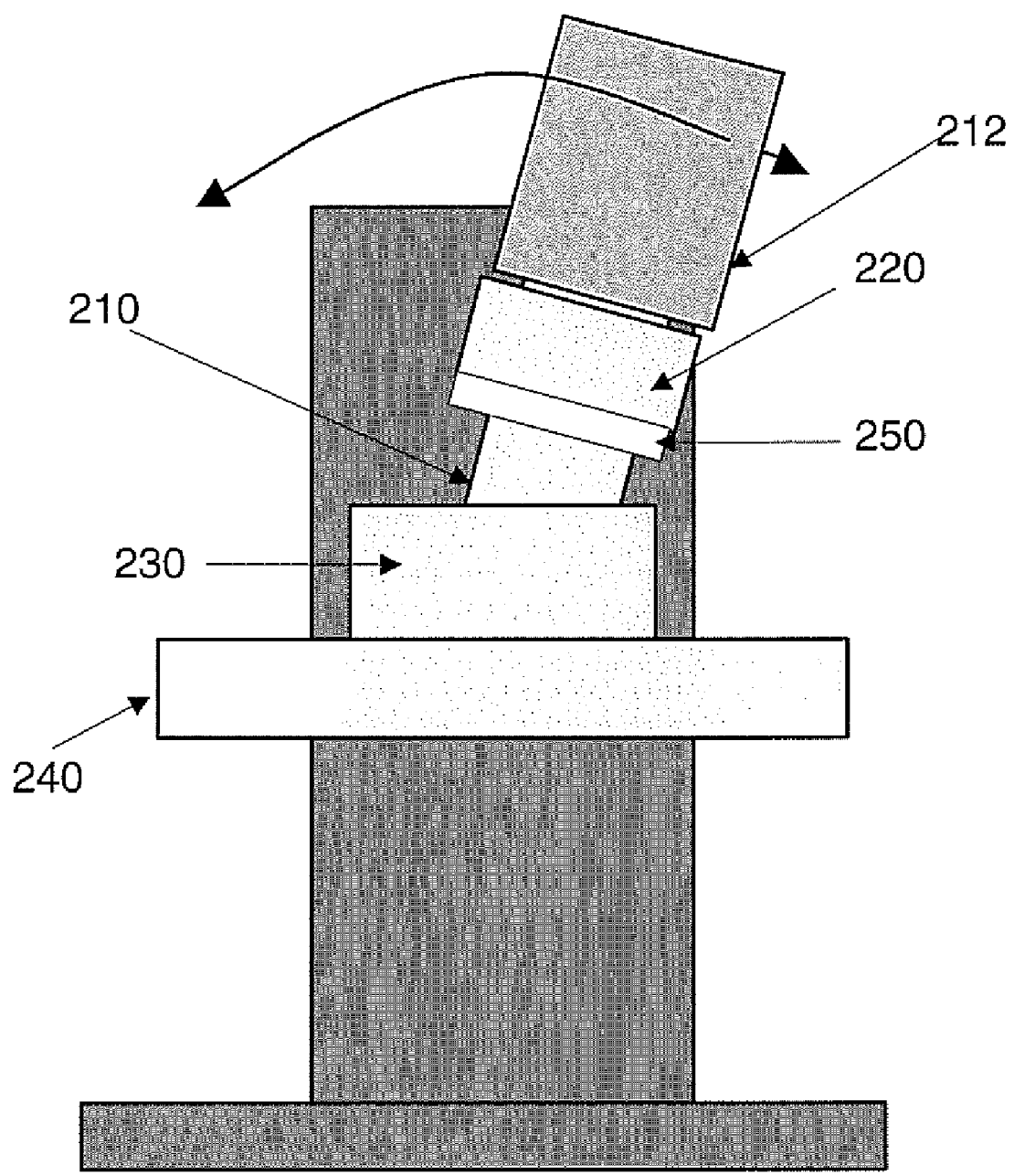
FIG. 2 is diagrammatic illustration of a mammography imaging system as described in an embodiment of the invention.

FIG. 2 is diagrammatic illustration of a mammography imaging system as described in an embodiment of the invention. The mammography imaging system comprises an image gantry 210, a compression mechanism 220 detachably connected to the image, gantry 210 and a breast holder 240. A breast biopsy device 230 or some other similar external device may be connected to the mammography system as and when a biopsy operation is required. The breast biopsy device 230 is connected to the breast holder 240. Upon detection of the breast biopsy device, the compression mechanism 220 is configured to automatically elevate its position, so that a collision between the breast biopsy device 230 and the compression mechanism 220 can be avoided. In an embodiment, a controlling mechanism 250 is provided in association with the compression mechanism 220 to facilitate the detection of the breast biopsy device 230 and to automatically position the compression mechanism 220. However the controlling mechanism 250 may be a part of the existing controlling mechanism or processor used in mammography system or it could be an external device.

The controlling mechanism 250 may also include a detection mechanism to detect the presence of the breast biopsy device 230 connected to or near to the mammography system. The detection mechanism may be an electrical signal based detection mechanism configured to detect the breast biopsy device 230 upon connecting the breast biopsy device 230 to the mammography system. Alternately, the detection mechanism may be a proximity sensor mechanism configured to detect the presence of the breast biopsy device 230 near to the mammography system. The mammography workflow, when a breast biopsy device is connected to the mammography system. The controller 250 may also include a signal generator configured to generate a trigger signal based on the detection of the presence of the breast biopsy device 230. The trigger signal may be used to retract the position of the compression mechanism 220. In an embodiment, the signal generator may generate a release signal upon disconnecting the breast biopsy device 230 from the mammography system. This could be used in controlling the further movements of the compression mechanism 220. Since the compression mechanism 220 is parked to the top most position, the chances of collision between the compression mechanism 220 and the breast biopsy device 230 is minimal.

Since the compression mechanism 220 is configured to move up automatically upon detection of a breast biopsy device 230, human intervention or manual adjustment is not required to control the position of the compression mechanism 220.

In an embodiment, after detecting the breast biopsy device automatically, the compression mechanism can be adjusted manually. Alternately, the presence of the breast biopsy device can be detected manually and the positioning of the compression mechanism can be done automatically.

Figure 3:
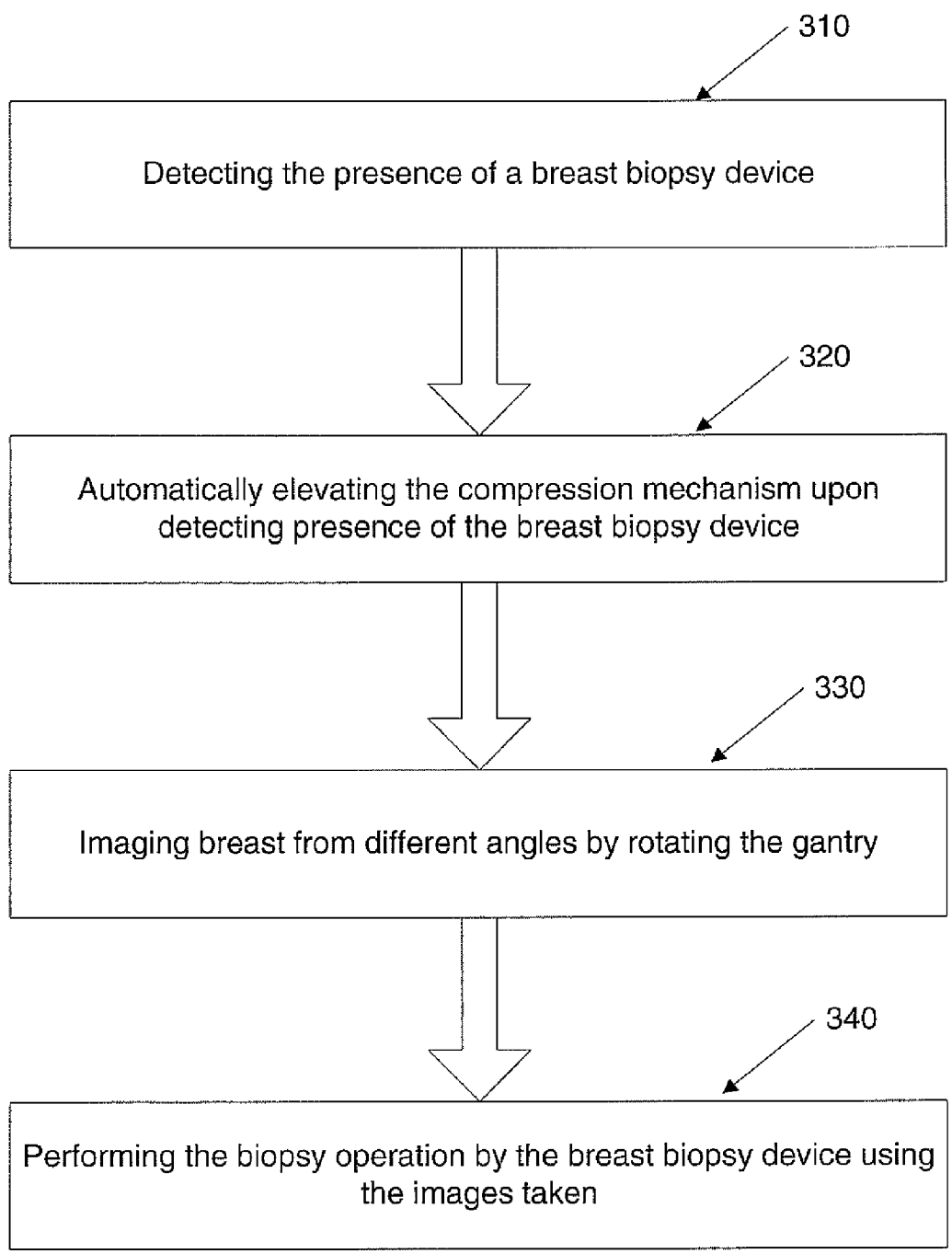
FIG. 3 is a flowchart illustrating a mammography biopsy workflow as described in an embodiment of the invention.

FIG. 3 is a flowchart illustrating a mammography biopsy workflow as described in an embodiment of the invention. At step 310, the presence of a breast biopsy device is detected. This can be detected manually or automatically. The presence of the breast biopsy device can be detected automatically, upon detecting the presence of the breast biopsy device near to the mammography system. Alternately, the breast biopsy device can be detected upon connecting the same to the mammography system. This detect signal may be used to control the position of a compression mechanism in the mammography system. At step 320, the detect signal is configured to trigger the compression mechanism to move upwards, so that while imaging or biopsy operation it does not come into the way of the breast biopsy device. The compression mechanism is moved automatically up and may be parked at the topmost location. However the elevated position of the compression mechanism can be configured based on various applications and requirements. The compression mechanism could be elevated upon connecting the breast biopsy device to the mammography system or upon detecting the same in proximity of the mammography system. The term "proximity" may be defined and set based on the requirement. For example, the compression mechanism may be elevated only when the breast biopsy device is very close to the mammography system, so that erroneous detection of breast biopsy device and movement of compression mechanism can be avoided. At step 330, the image gantry of the mammography system is rotated and various images of the breast from different angles are taken. In an example, one Scout image and two angular images are taken to perform a steriostatic breast biopsy operation. When the image gantry rotates, the compression mechanism associated with the image gantry also rotates. However since the compression mechanism is in an elevated position, it does not interfere with the breast biopsy device. At step 340, the biopsy operation is performed by the breast biopsy device using the images taken. With reference to the images taken, the position of the puncture needle that needs to be entered to perform the biopsy operation is decided Since the positioning of the compression mechanism is done before the biopsy operation, the chances of breast misalignment or movement is less and this ensures more accurate biopsy operation.

Figure 4:
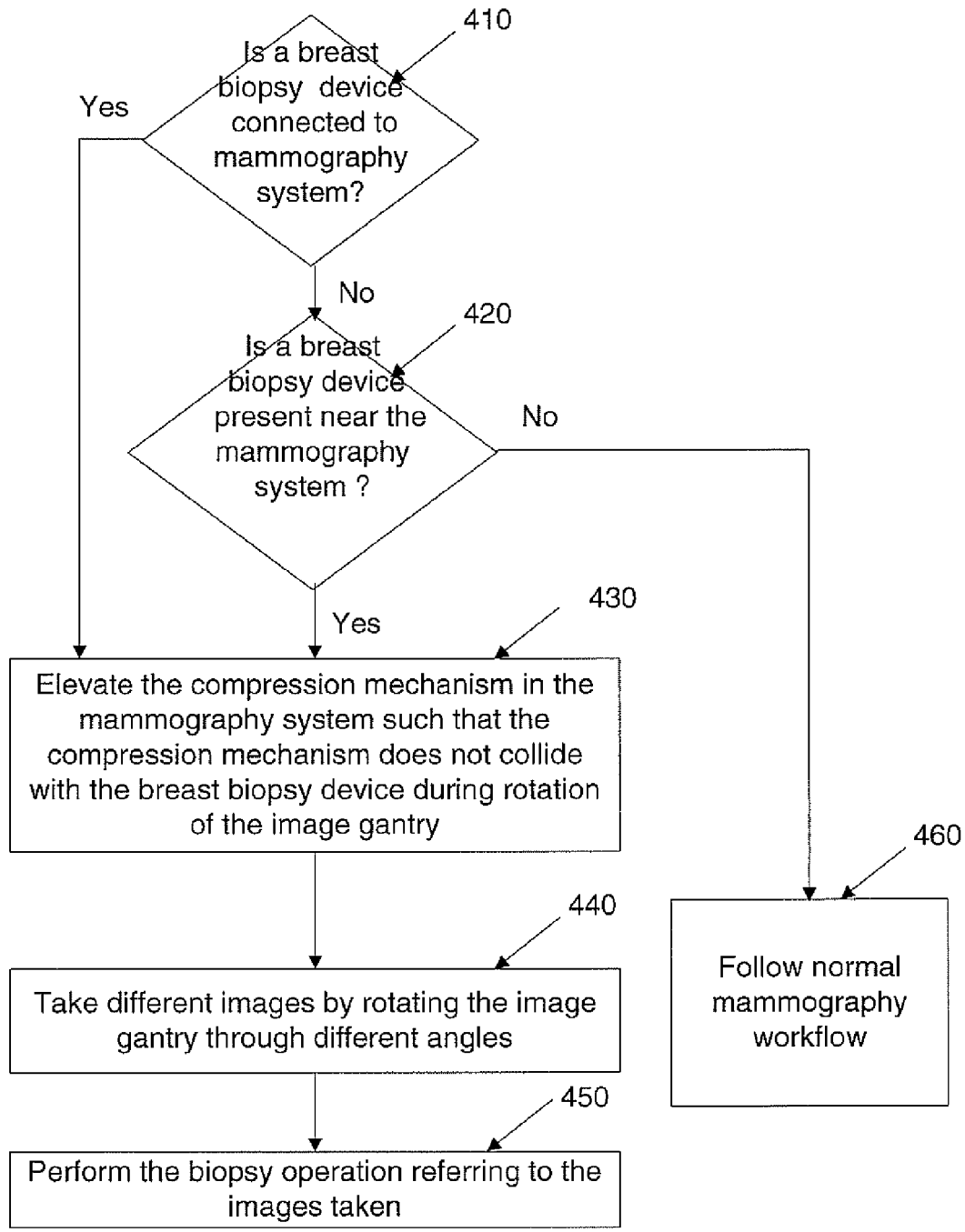
FIG. 4 is a flowchart illustrating a detailed mammography biopsy workflow as described in an embodiment of the invention.

FIG. 4 is a flowchart illustrating detailed mammography biopsy workflow as described in an embodiment of the invention. At step 410, a check is made to identify whether any breast biopsy device is connected to the mammography system. In an embodiment, this is done by checking the connector at which the breast biopsy device is connected or from the electrical signal generated by the breast biopsy device upon connection of the same to the mammography system. If the breast biopsy device is connected to the system, the compression mechanism may be elevated automatically as at step 430. If the breast biopsy device is not connected to the mammography system, another check is made to check whether there is any the breast biopsy device near to the mammography system as at step 420. If there is a breast biopsy device near to the mammography system, the compression mechanism is elevated automatically as at step 430. If no breast biopsy device is detected near to the mammography system, the mammography system is configured to perform the normal workflow as at step 460. Once the compression mechanism is elevated automatically to a desired location as at step 430, image gantry is rotated and images are taken from different angles as at step 440. Step 440 is performed upon making sure that the compression mechanism does not interfere with the breast biopsy device. Once the images are taken, the breast biopsy device performs biopsy operation referring to the images taken as at step 450.

Figure 5:
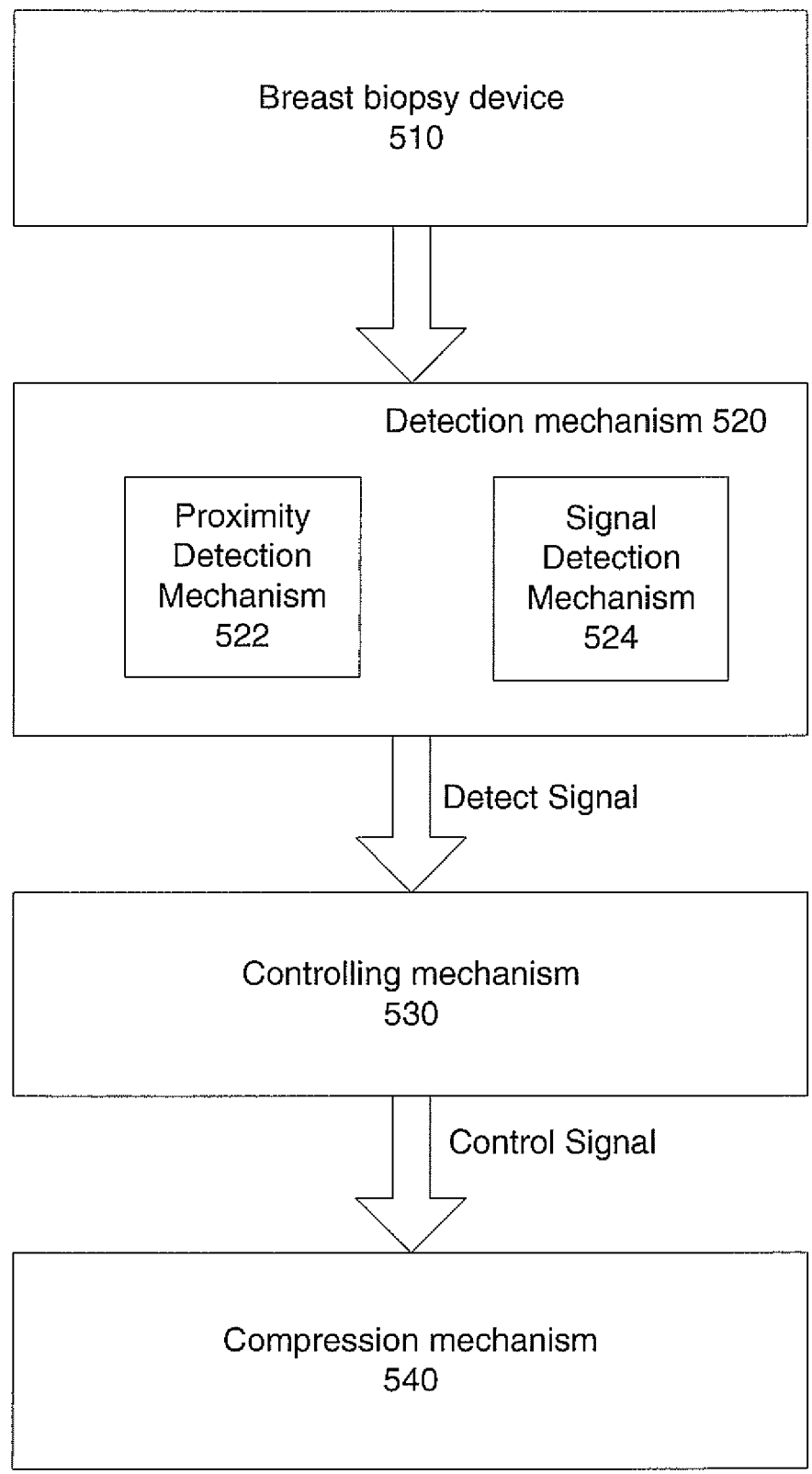
FIG. 5 is diagrammatic illustration of a positioning mechanism for a compression mechanism in a mammography imaging system as described in an embodiment of the invention.

FIG. 5 is diagrammatic illustration of a positioning mechanism for a breast handling mechanism in a mammography imaging system as described in an embodiment of the invention. The positioning mechanism is shown in association with the breast biopsy device 510 and the compression mechanism 540. The positioning mechanism may be a part of the mammography system or may be a part of the breast biopsy device 510. However the positioning mechanism may be a device external to both the compression mechanism 540 as well as the breast biopsy device 510. In an embodiment, the breast biopsy device 510 is associated with a detection mechanism 520, which is configured to detect the presence of the breast biopsy device 510. In an embodiment, the detection mechanism is a proximity detection mechanism 522, which could be used to detect the breast biopsy device 510 even before connecting the same to the mammography system. In an embodiment, a proximity sensor such as RFD (Radio frequency identifier) or any other similar devices may be attached with the breast biopsy device 510 and an RFID detector may be connected to the mammography system, thereby the presence of the breast biopsy device 510 near to the mammography system can be identified. Alternately, a signal detection mechanism 524 may be provided. This may detect the signal generated by breast biopsy device 510 or by a connector upon connecting a breast biopsy device 510 to the mammography system. The breast biopsy device 510 may also be detected by checking the connector or place at which the breast biopsy device 510 is connected. In an embodiment, the breast biopsy device 510 is connected to a breast holder, which is configured to hold the breast while imaging.

The output of the detection mechanism 520 is a detect signal which is fed to a control mechanism 530. The control mechanism 530 is configured to control the position of the compression mechanism 540 automatically. A control signal generated by the control mechanism 530 is configured to trigger the compression mechanism 540 to move upwards and park it at the top most position. However, the parking position of the compression mechanism 540 can be configured based on the application and requirement.

In an embodiment, the detect signal from the detection mechanism 520 may indicate the removal of breast biopsy device 510 from the mammography system. Then the control mechanism 530 may generate a retract signal to retract the compression mechanism 540 to its original position. However the retract position of the compression or the automation of retracting the compression mechanism 540 to its original position may be configured based on the application.

Figure 6:
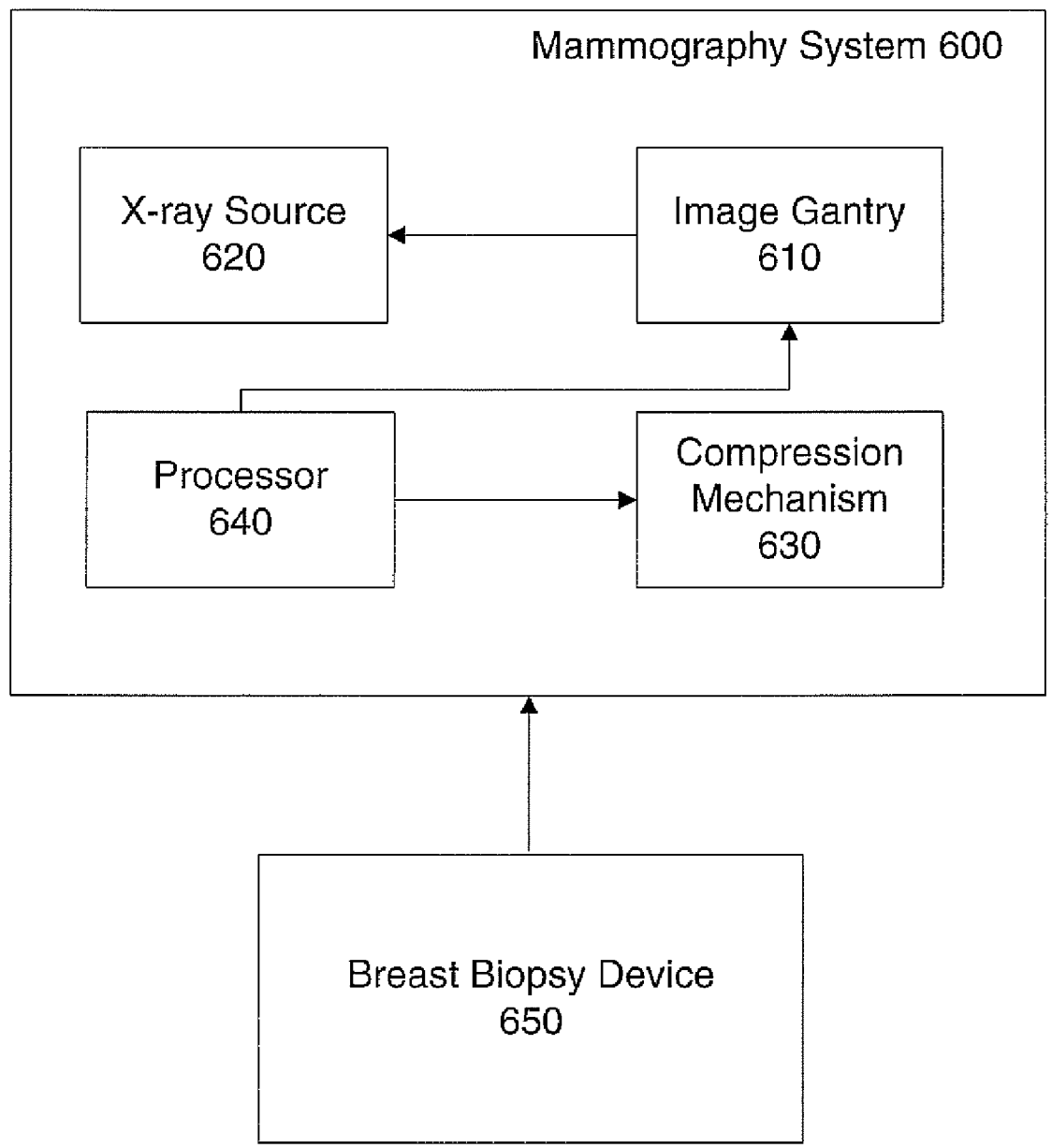
FIG. 6 is block diagram of a mammography imaging system as described in an embodiment of the invention.

FIG. 6 is block diagram of a mammography imaging system as described in an embodiment of the invention. The mammography system 600 is configured to include an image gantry 610 in association with an X-ray source 620, a compression mechanism 630 and a processor 640 to control the operation of the mammography system 600. A detachable breast biopsy device 650 is connected to the mammography system 600 for performing biopsy operation. The image gantry 610 along with the X-ray source 620 rotate while imaging to acquire images of the breast from different angles. The compression mechanism 630 is associated with the image gantry 610 and it moves along with the image gantry movement. The compression mechanism 630 is adjustably connected to the image gantry 610. The processor 640 is configured to control the imaging operation performed by the mammography system 600.

The breast biopsy device 650 such as a Stereotactic breast biopsy device is connected to the mammography system as and when a biopsy operation is required.

In an embodiment, the processor 640 is further configured to detect the presence of the breast biopsy device 650. The processor 640 may identify the breast biopsy device 650 upon connecting the same to the mammography system 600. Alternately with the help of proximity sensing devices, the presence of the breast biopsy device 650 near to the mammography system 600 can be detected. Based on the presence of breast biopsy device 600, the processor 640 may generate a signal to elevate the compression mechanism 630 to a suitable position. The elevated position of the compression mechanism 630 can be configured based on the application and requirement. In an example, the compression mechanism 630 is parked to the top most position.

In an embodiment, after elevating the compression mechanism 630 to suitable position, it may be locked. This will avoid the free fall of the compression mechanism 630 during biopsy operation.

In an embodiment, the processor 640 may also detect the removal of the breast biopsy device 650 from the mammography system 600. Upon removal of the breast biopsy device 650, the processor 640 may generate a signal to retract the compression mechanism 630 to it original position. However this is an optional feature and the retracted position can be decided based on requirements. Alternately, the retract signal may trigger an alarm indicating that the compression mechanism 630 may be retracted to its original position and the operator may manually position the compression mechanism 630 to its original position.

Even though the processor 640 is shown as an integral part of the mammography system 600, different configuration of the processor 640 such as processor 640 associated with breast biopsy device 650 or to any external device can be used. The processor 640 can be any computer processor configured to generate a signal to elevate the position of the compression mechanism 630 upon detection of a breast biopsy device 650. The processor 640 may include personal computers, hand-held devices, multi-processor systems, microprocessor-based or programmable consumer electronics, network PCs, minicomputers, mainframe computers, and the like.

The advantages of the invention include providing a safer mammography system, which ensures enhanced patient safety and prevents physical damage of the mammography system or breast biopsy device. Thus the invention improves the mammography workflow. The productivity of the system can be increased and the time for which the patient needs to be compressed can be reduced.

The automation ensures precise calculations of the positions where the puncture needle must enter the breast during biopsy operation and the depth it should go when biopsy is initiated.

By using the invention the mammography system is made safer to operate, intelligent enough to auto position and prevent any physical damages while in operation. Also this results in workflow improvements resulting in relief to the operator and patient.

Further enhanced patient safety is achieved by preventing any accidental possibilities of collisions between the compression mechanism and the breast biopsy device. This is especially important to prevent accidents during imaging operations and biopsy operations.

The operator mistakes and accidents can be avoided by auto positioning the compression mechanism. Further manual interventions and the need for the operator to walk up to the image gantry to adjust positioning of the compression mechanism can be avoided and this saves precious workflow moments.

Since the positioning of the compression mechanism is done before the biopsy operation, the chances of patient movement during the biopsy operation are minimal and hence the biopsy operation can be performed more accurately. Further the patent is free from scare as the sound of adjusting the compression mechanism after the patient being positioned for biopsy can be can be avoided. This also adds much more convenience to the patients.

The above-description of the embodiments of the methods and systems has the technical effect of automatically positioning the compression mechanism in a mammography system upon detection of breast biopsy device.

Thus various embodiments of the invention describe a method and system for automatically positioning the compression mechanism based on the detection of a breast biopsy device in a mammography imaging procedure.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments are described above in detail. The assemblies and methods are not limited to the specific embodiments described herein, but rather, components of each assembly and/or method may be utilized independently and separately from other components described herein. Further the steps involved in the workflow need not follow the sequence in which there are illustrated in figures and all the steps in the work flow need not be performed necessarily to complete the method.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A breast biopsy workflow in a mammography system having a compression mechanism and a rotatable image gantry comprises:
   detecting the presence of a breast biopsy device;
   automatically elevating the compression mechanism upon detecting the presence of the breast biopsy device;
   imaging breast from different angles by rotating the image gantry; and
   performing a biopsy operation with the breast biopsy device.

2. A method as claimed in claim 1, wherein the step of detecting comprises:
   identifying the presence of the breast biopsy device near the mammography system.

3. A method as claimed in claim 1, wherein the step of detecting comprises:
   identifying the breast biopsy device connected to the mammography system.

4. A method as claimed in claim 1, wherein the step of imaging comprises:
   acquiring at least one scout image and two angular images.

5. A positioning mechanism for a compression mechanism in a mammography imaging system comprises:
   a detection mechanism configured to detect the presence of a breast biopsy device; and
   a controlling mechanism connected to the detection mechanism, configured to control the position of the compression mechanism based on the output of the detection mechanism;
   wherein the controlling mechanism is further configured to generate a release signal to retract the compression mechanism upon disconnecting the breast biopsy device from the mammography system.

6. A mechanism as claimed in claim 5, wherein the detection mechanism is configured to detect the breast biopsy device connected to the mammography system.

7. A mechanism as claimed in claim 5, wherein the detection mechanism includes a proximity sensor configured to detect the breast biopsy device connected to the mammography system.

8. A mechanism as claimed in claim 5, wherein the controlling mechanism is configured to receive a detect signal from the detection mechanism and generate a trigger signal to control the position of the compression mechanism.

9. A mechanism as claimed in claim 5, wherein the breast biopsy device is a Stereotactic breast biopsy device.

10. A mammography imaging system with a rotatable image gantry having an X-ray source comprises:
    an adjustable compression mechanism connected to the image gantry;
    a detachable breast biopsy device attachable to the system; and a processor configured to automatically elevate the compression mechanism upon detecting the presence of the breast biopsy device and retract the compression mechanism upon removing the breast biopsy device from the mammography system.

11. A system as claimed in claim 10, wherein the compression mechanism includes: breast compressor, breast holding paddles and paddle holders.

12. A system as claimed in claim 10, wherein the processor is configured to detect the presence and absence of breast biopsy device.

13. A system as claimed in claim 10, wherein the elevated and retracted position of the compression mechanism is configurable.

* * * * *